US008033978B2

(12) United States Patent
Mick et al.

(10) Patent No.: US 8,033,978 B2
(45) Date of Patent: Oct. 11, 2011

(54) RADIO-NUCLEAR MATERIAL DELIVERY SYSTEM

(75) Inventors: Felix W. Mick, Bronxville, NY (US); Kenneth Zabrouski, Bethpage, NY (US)

(73) Assignee: Mick Radio-Nuclear Instruments, Inc., Mt. Vernon, NY (US)

( * ) Notice: Subject to any disclaimer, the term of this patent is extended or adjusted under 35 U.S.C. 154(b) by 1037 days.

(21) Appl. No.: 11/398,973

(22) Filed: Apr. 5, 2006

(65) Prior Publication Data
US 2007/0260197 A1    Nov. 8, 2007

(51) Int. Cl.
*A61N 5/00* (2006.01)
(52) U.S. Cl. .......................................................... 600/3
(58) Field of Classification Search .................. 600/1–8; 604/425; 250/506.1; 206/364
See application file for complete search history.

(56) References Cited

U.S. PATENT DOCUMENTS

| 4,056,096 A * | 11/1977 | Collica et al. ............. 600/5 |
| 2003/0141210 A1 * | 7/2003 | Yanke et al. .............. 206/364 |
| 2004/0242953 A1 * | 12/2004 | Good .......................... 600/7 |
| 2005/0080314 A1 | 4/2005 | Terwilliger et al. |
| 2007/0112310 A1 * | 5/2007 | Lavi et al. ................. 604/245 |

FOREIGN PATENT DOCUMENTS

| EP | 1 402 922 | 3/2004 |
| WO | 2006/014701 | 2/2006 |

OTHER PUBLICATIONS

European Supplementary Search Report dated Jul. 14, 2010, issued in corresponding European Patent Application No. 07867058.5.
Roth, et al., "*High dose rate intraoperative radiotherapy for recurrent cervical cancer and nodal disease,*" Gynecologic Oncology 91(1):258-260 (2003).
Beddar, et al., "*The optimization of dose delivery for intraoperative high-dose-rate radiation therapy using curved HAM applicators,*" Radiotherapy and Oncology 78(2): 207-212 (2006).

* cited by examiner

*Primary Examiner* — Charles A Marmor, II
*Assistant Examiner* — Christine Hopkins
(74) *Attorney, Agent, or Firm* — Kenyon & Kenyon LLP

(57) ABSTRACT

A radio-nuclear material delivery system includes: a body; at least one catheter including a portion arranged within the body and extending along a longitudinal length of the body, each catheter including a blind lumen in which a radioactive material is insertable; and a shield arranged on an exterior of the body and movable along the body in a longitudinal direction of the catheter. The shield may be made of a tungsten material, e.g., coated with titanium nitride, for attenuating radiation from the nuclear material and controlling dosing of radiation for treatment of, e.g., breast cancer.

21 Claims, 14 Drawing Sheets

RADIO-NUCLEAR MATERIAL DELIVERY SYSTEM

FIELD OF THE INVENTION

The present invention relates to a radio-nuclear material delivery system.

BACKGROUND INFORMATION

Radio-nuclear material delivery systems provide radioactive materials to patients who require treatment for a variety of illnesses or conditions, such as cancer. These delivery systems provide for delivery of radio-nuclear material in proximity to, e.g., cancerous tissues, so that the radio-nuclear material may destroy the cancer cells.

SUMMARY

According to an example embodiment of the present invention, a system includes: a body; at least one catheter including a portion arranged within the body and extending along a longitudinal length of the body, each catheter including a blind lumen in which a radioactive material is insertable; and a shield arranged on an exterior of the body and movable along the body in a longitudinal direction of the catheter.

The shield may be formed of a tungsten material.

The shield may include a TiN finish.

The at least one catheter may include a plurality of catheters arranged in a linear array along a width of the body.

The catheters may be equally spaced along the width of the body.

The body may be formed of a synthetic material.

The system may include an end shield arranged on a distal end of the body.

The end shield may be formed of a tungsten material.

The end shield may include a TiN finish.

The catheter may include a tube portion plugged at a distal end.

The catheter may include an anchor device at a distal end adapted to anchor the catheter in the body.

The catheter may be connectible to a loading device adapted to load the radioactive material into the catheter.

The body may include a scale arranged along the longitudinal length adapted to indicate a position of the shield along the longitudinal length.

Further aspects and features of example embodiments of the present invention are explained in further detail below with reference to the appended Figures.

DETAILED DESCRIPTION

Figure 1:
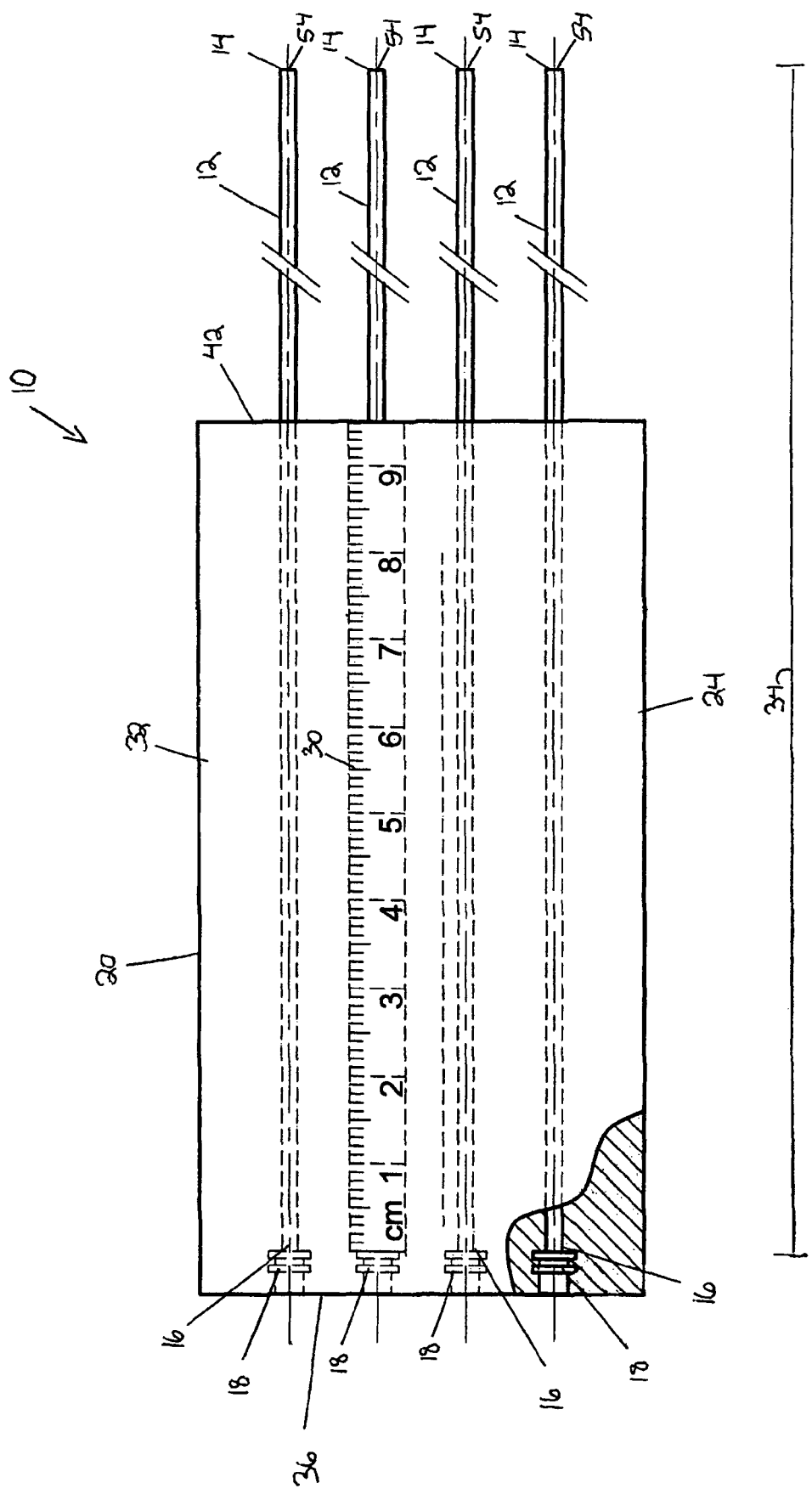
FIG. 1 is a top view of a radio-nuclear delivery system according to an example embodiment of the present invention.
Figure 1A:
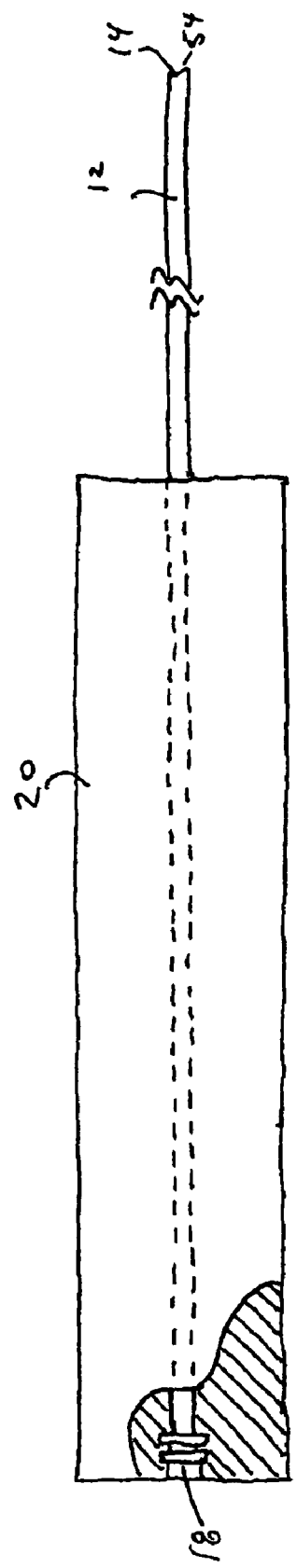
FIG. 1A is a side view of the system illustrated in FIG. 1.

FIG. 1 is a top view of a radio-nuclear delivery system 10, and FIG. 1A is a side view of the system 10. The system 10 is arranged an apparatus to deliver radioactive materials, such as radioactive seeds, to a treatment site of a patient, e.g., a patient's breast for the treatment of breast cancer. The system 10 includes body 20 which houses components of the system 10. Catheters 12 which carry the radioactive materials are placed, at least partially, within the body 20. Although four catheters 12 are illustrated, any number of catheters 12 may be provided. For example, one to ten catheters 12, or channels, may be provided, depending upon, e.g., the application or treatment needs. The catheters 12 may be made of any material to allow delivery of the radio-nuclear material to the treatment site. For example, the catheters 12 may be made of Celcon material (NS12048), e.g., 130 centimeters in length, having an outside diameter of, e.g., 0.18 centimeters, and an inside diameter of, e.g., 0.132 centimeters. As illustrated in FIG. 1, the body 20 partially encloses the catheters 12, e.g., the distal ends of the catheters 12, since the body 20 may have a length of, e.g., 10 centimeters.

The body 20 may be formed of a bio-compatible, synthetic material, e.g., a medical grade silicone rubber, e.g., Silpak R2310MA/B.

The catheters 12 are tube-shaped to allow a radioactive element to be delivered to its distal end located within the body 20. Each catheter 12 has a first end 14, e.g., a proximal end, and a second end 16, e.g., a distal end. At the distal end 16, a button 18 is arranged to provide a connection point between the catheter 12 and the body 20. The amount or relative position of the radioactive material along the length 34 of the catheter 12 may be measured by a scale 30. The body 20 has a distal end 36 and a proximal end 42. Thus, the radioactive material is delivered to a desired location along the length of the body 20 between the proximal end 42 and the distal end 36 by loading the radioactive material into the catheters 12 with a loading system.

Figure 9:
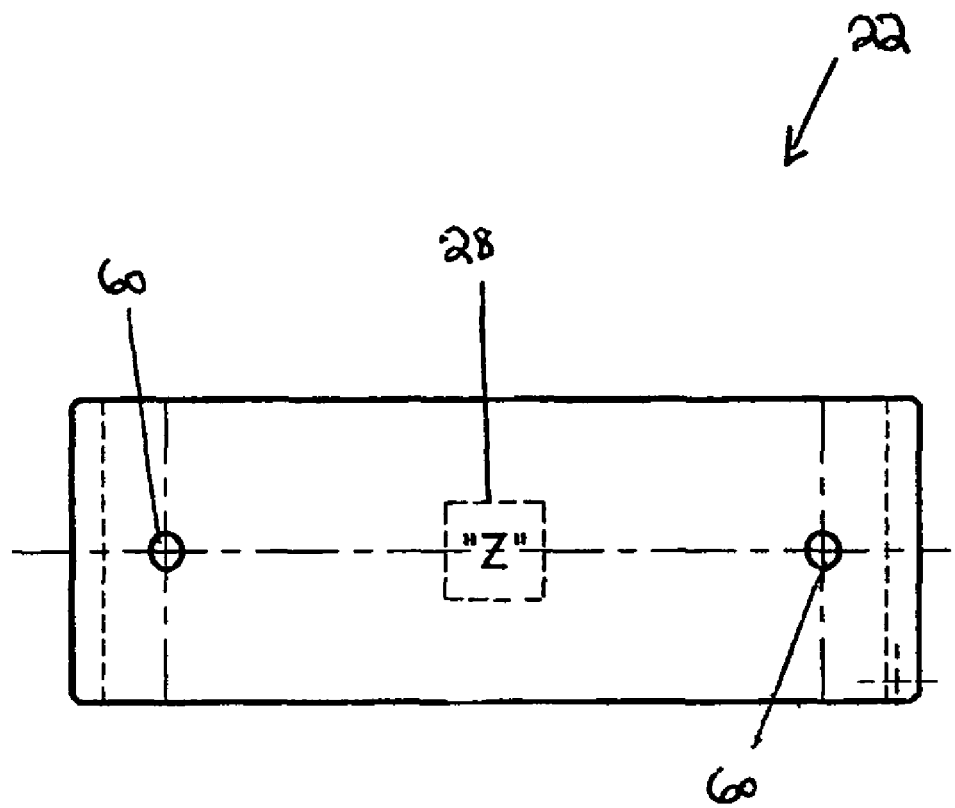
FIG. 9 is a top view of a shield for a body of the system illustrated in FIG. 1.
Figure 10:
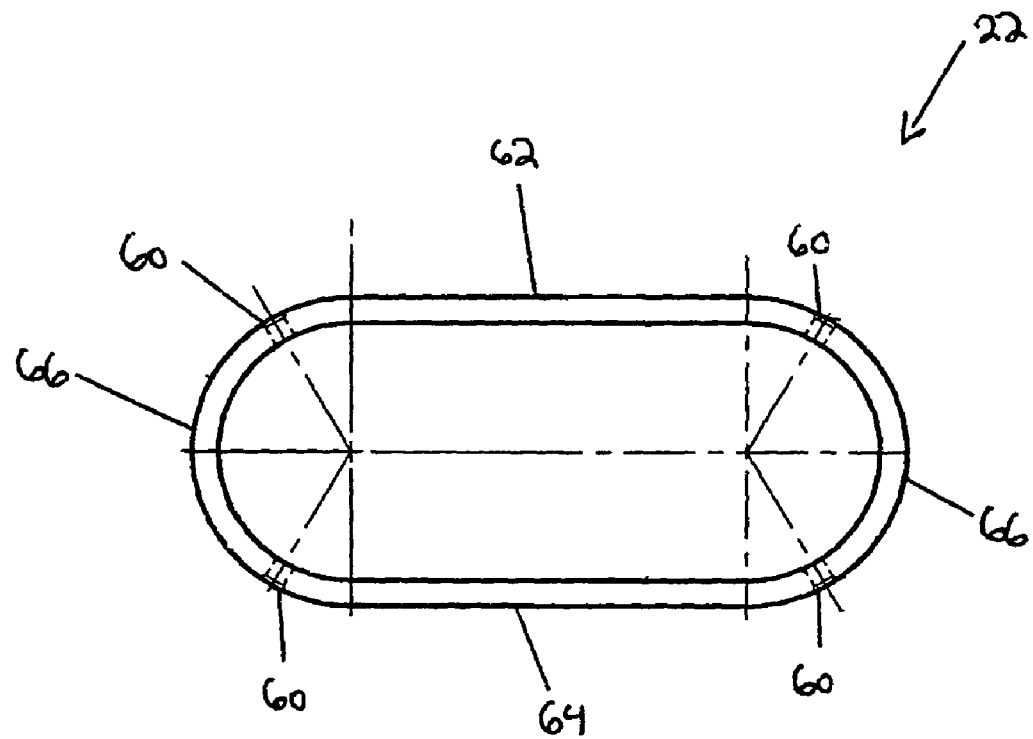
FIG. 10 is an end view of the shield illustrated in FIG. 9.
Figure 11:
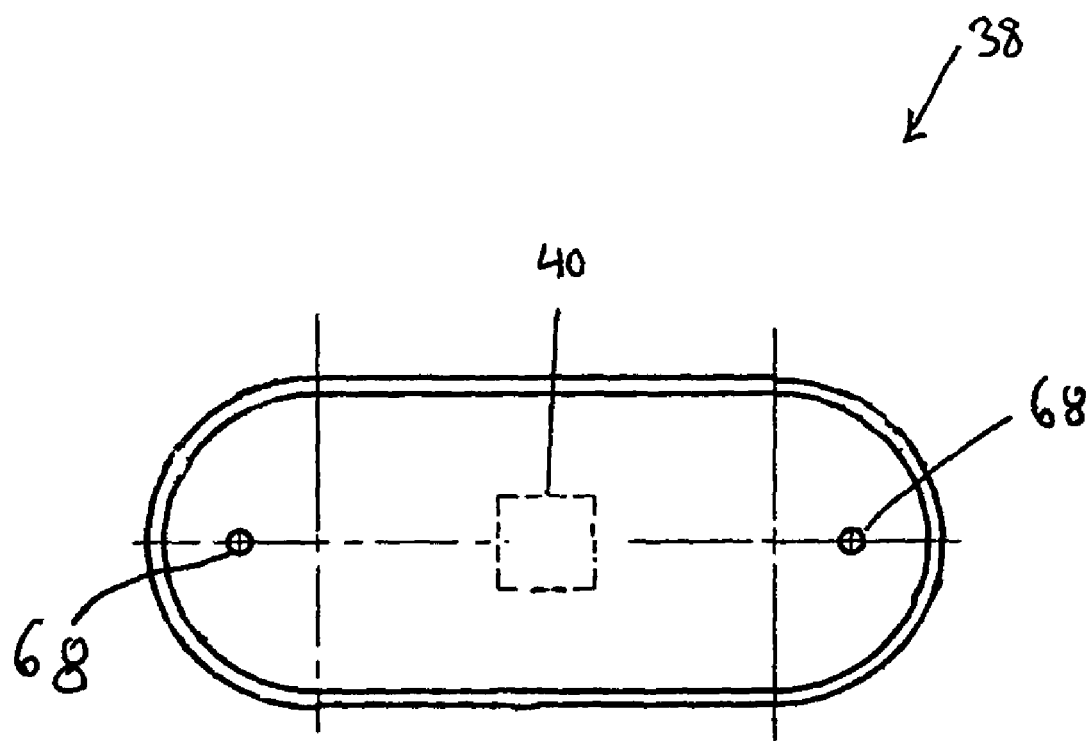
FIG. 11 is an end view of a distal end shield for the system illustrated in FIG. 1.
Figure 12:
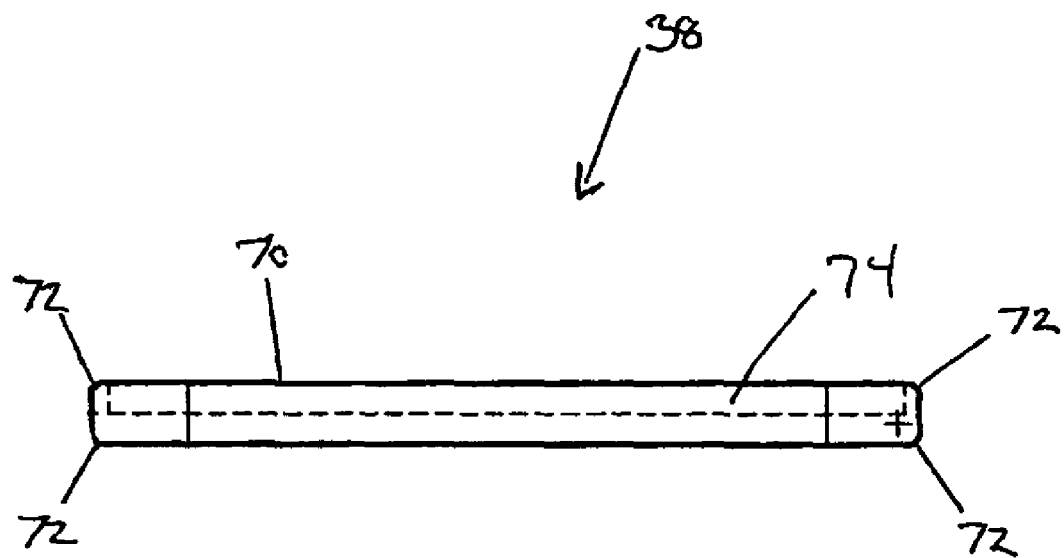
FIG. 12 is a top view of a distal end shield illustrated in FIG. 11.

A distal end shield 38, such as that illustrated in FIGS. 11 and 12, may be provided on the distal end 36 of the body 20, and a shield 22, such as that illustrated in FIGS. 9 and 10, may be provided, e.g., movably, along the length of the body 20 between the distal end 36 and the proximal end 42. The shields may be provided to permit desired shielding and further control of the dosing of radiation by the radioactive material. For example, the shield 22 and/or the distal end shield 38 may be formed of, e.g., a tungsten material, having a composition of, e.g., 90% W, 6% Ni and 4% Cu. The shield 22 and/or the distal end shield 38 may include a coating that allows the shield 22 and/or the distal end shield 38 to be placed in contact with the patient's body without or with minimal or reduced negative effects. For example, the coating may be titanium nitride. A titanium porous coating, such as titanium nitride, may provide for biocompatibility. Titanium porous coatings may be provided by high ionization deposition. The use of titanium nitride based coatings may provide, for example, increased hardness value, e.g., 2400 HV (Vickers), as compared to 900 HV (Vickers) for hard chromium materials. Additionally, titanium nitride may reduce friction, is believed to be chemically inert and may provide acceptable heat tolerance limit.

As mentioned above, the overall length of the body 20 may be, e.g., 10.00 centimeters. The width of the body 20, e.g., in the direction into the page in the view of FIG. 1, may be, e.g., 2 centimeters, and the width of the body 20 may depend on the number of catheters 12, or channels, provided. A center-to-center distance between the catheters 12 may be, e.g., 1.0 centimeter. The center-to-center distance between outer-most catheters 12 and the overall width of the body 20 in relation to the number of catheters 12, or channels, may be as set forth below:

| Number of Channels | Center-to-Center Distance Between Outermost Catheters 12, Channels (cm) | Overall Width of Body 20 (cm) |
| --- | --- | --- |
| 2 | 1.0 | 3.0 |
| 3 | 2.0 | 4.0 |
| 4 | 3.0 | 5.0 |
| 5 | 4.0 | 6.0 |
| 6 | 5.0 | 7.0 |
| 7 | 6.0 | 8.0 |
| 8 | 7.0 | 9.0 |
| 9 | 8.0 | 10.0 |
| 10 | 9.0 | 11.0 |

Figure 2:
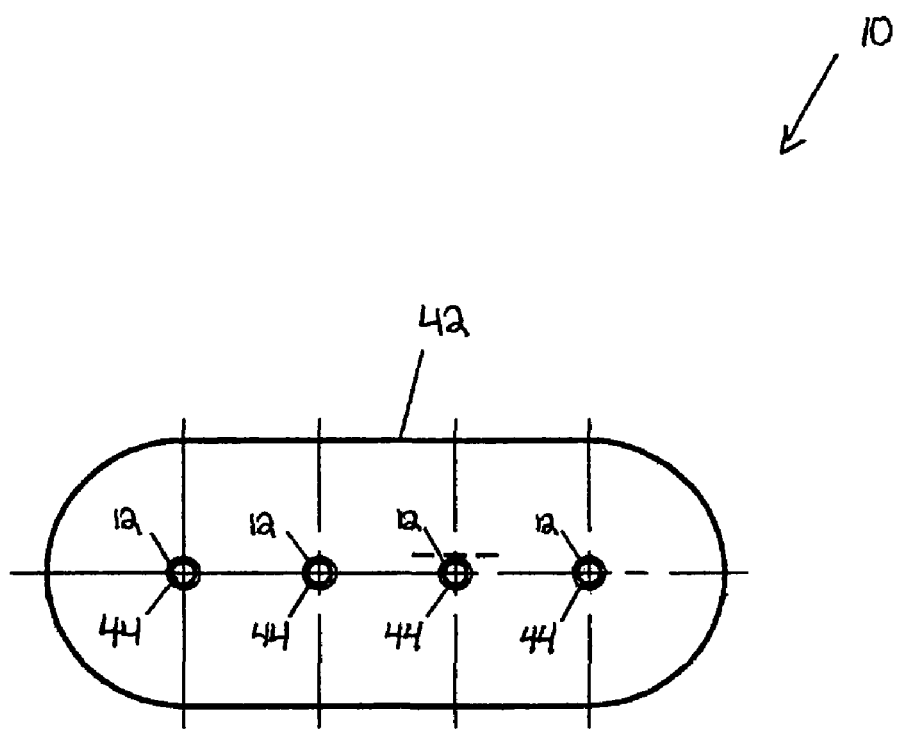
FIG. 2 is an end view of the system illustrated in FIG. 1.

FIG. 2 is an end view of the system 10 and illustrates the arrangement of the catheters 12 and body 20.

Figure 3:
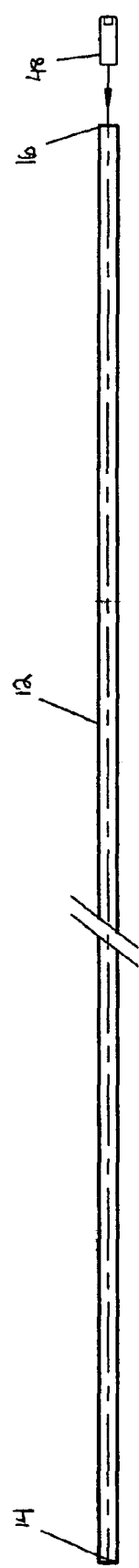
FIG. 3 is an exploded view of a catheter subassembly of the system illustrated in FIG. 1.

FIG. 3 is an exploded view of a catheter subassembly. The catheter 12 has a tube portion with a proximal end 14 and a distal end 16. A plug, e.g., a set screw 48, is inserted into the tube portion at the distal end 16. The set screw 48 is friction fit into the body of the catheter 12 to prevent removal of the set screw 48 from the second end 16. The set screw 48 may be made from a metallic material to provide durability, e.g., stainless steel, and the surface of the set screw 48 may be provided with a bioacceptable coating to minimize adverse reactions with patients.

Figure 4:
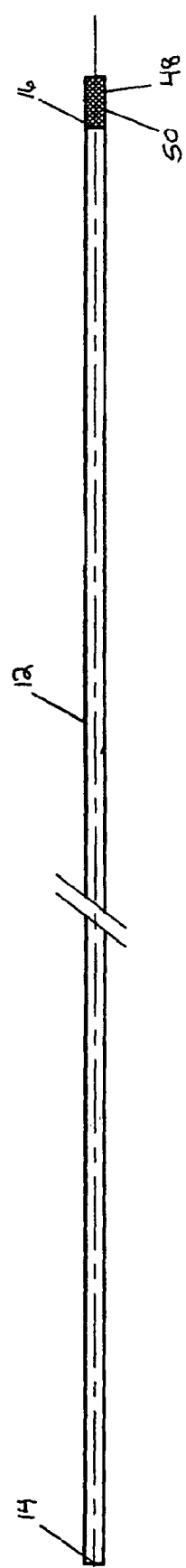
FIG. 4 is a top view of the catheter subassembly illustrated in FIG. 3.
Figure 5:
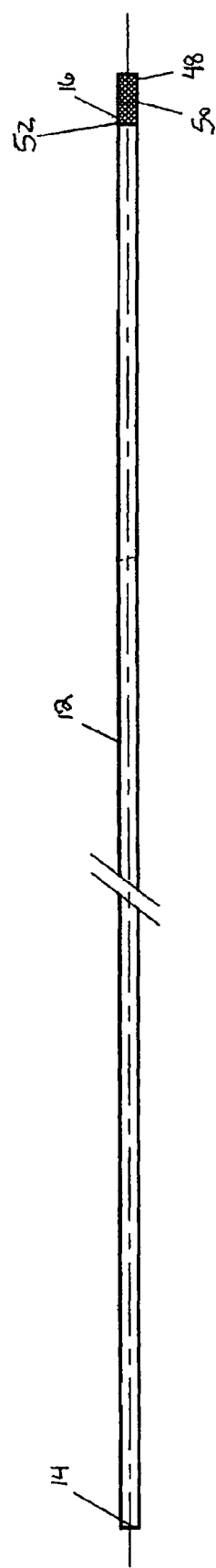
FIG. 5 is a top view of the catheter subassembly illustrated in FIGS. 3 and 4.
Figure 6:
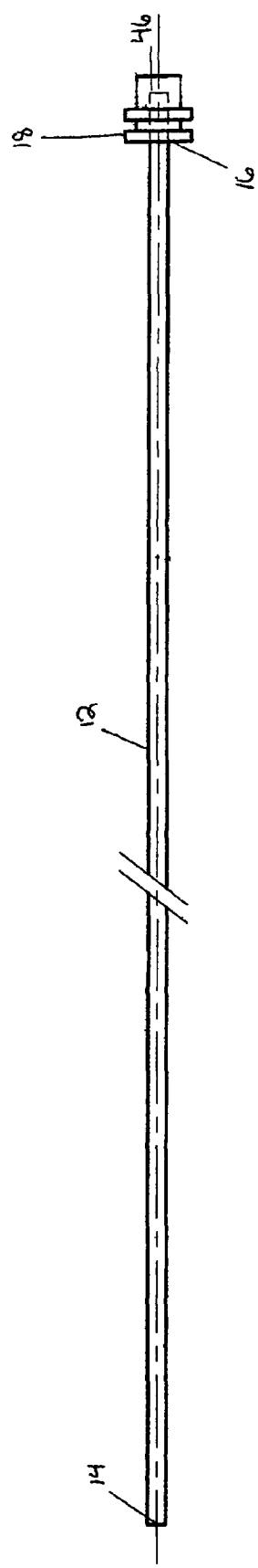
FIG. 6 is a top view of a catheter assembly of the system illustrated in FIG. 1.

Referring to FIG. 4, a portion 50 of the distal end 16 of the may be abraded, e.g., after insertion of the set screw 48, to provide a roughened surface along, e.g., the distal-most 3/16 inches of the tube portion 12. The abrading may be accomplished, e.g., mechanically, chemically, etc. An adhesive 52, as illustrated in FIG. 5, may be applied to the portion 50 along the, e.g., 3/16 inch length of the abraded surface. The adhesive 52, e.g., a single drop of Loctite #401, is applied in a sufficient quantity to attach a button 18 to the distal end 16. FIG. 6 illustrates a complete assembly of the catheter 12 with the button 18. The button 18 is permanently affixed to the distal end 16 of the tube portion to withstand, e.g., a four pound pull test.

Figure 7:
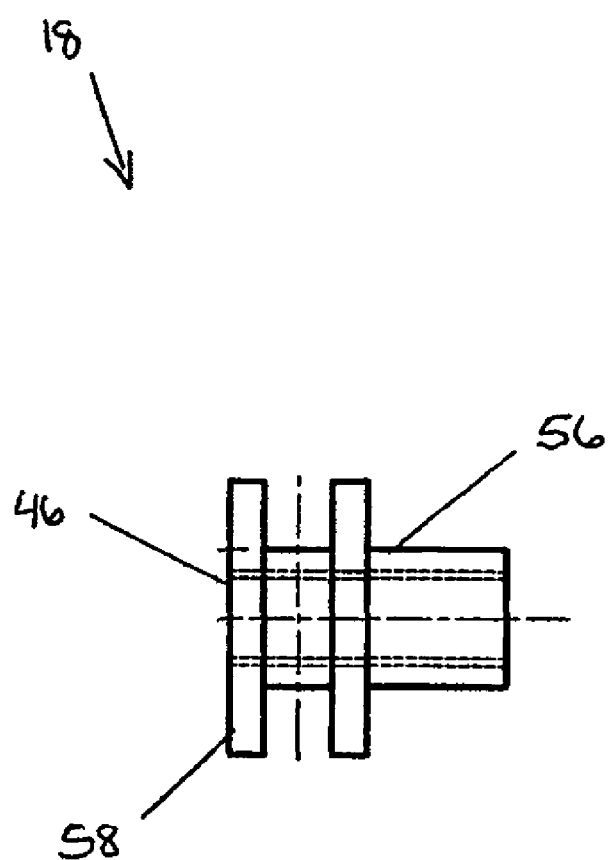
FIG. 7 is top view of an end button of the catheter assembly illustrated in FIG. 6.
Figure 8:
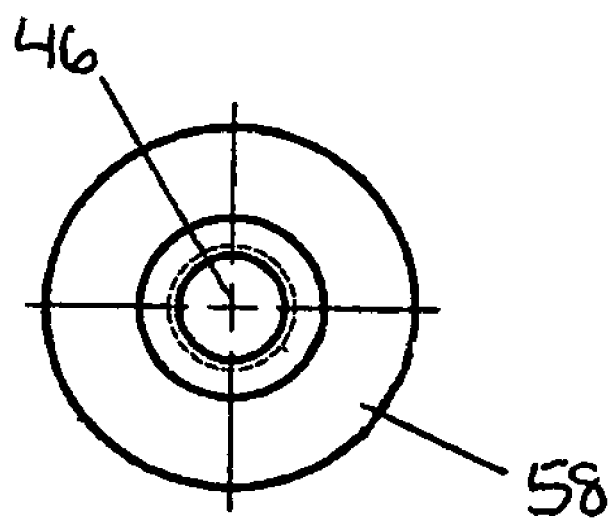
FIG. 8 is an end view of the end button illustrated in FIG. 7.

FIGS. 7 and 8 illustrate the button 18 in further detail. The button 18 includes a through-hole 46, which may be threaded. One or more spool portions 58 are provided to allow for connection and secure anchoring of the button in the body 20. The button 18 is made of a metallic material, e.g., as tungsten, magnesium, stainless steel, etc., or a plastic or synthetic material, e.g., Delrin. The exterior surface of the button 18 may include a biocompatible coating to minimizing or limit potential adverse reactions of a patient.

FIG. 9 is a top view of a shield 22 which may, e.g., movably, arranged on an outside of the body 20 to provide for shielding to increase the ability to control and appropriately treat cancerous tissue with the radioactive material. The shield 22 may be provided with an identification marking 28 to indicate number of channels of the system with which the shield 22 is to be used. Holes 60 may be provided in the shield 22. The movable shield 22 is positioned around the body 20 to provide full-circumference shielding and is movable along the length of the body 20. The scale 30 is used to position the shield 22. Based on the position of the shield 22 relative to the radioactive material in the catheters 12, the dosing and treatment of the cancerous tissue may controlled. As described above, the shield 22 may be made of a tungsten material having a TiN finish (e.g., 0.0002 in.). It FIG. 10 is an end view of the shield 22. As illustrated in FIG. 10, the interior of the shield 22 may have a geometry that is complementary to the exterior geometry of the body 20. For example, the shield 22 illustrated in FIG. 10 includes parallel sides 62, 64 connected by rounded ends 66. The shield 22 may have a thickness of, e.g., 2.0 mm The shield 22 may include holes for suturing the shield 22 in place at the treatment site.

FIGS. 11 and 12 illustrates the distal end shield 38, which may be provided on the distal end 36 of the body 20. The distal end shield 36 may be formed of a plate 70 of tungsten material (e.g., 90% W, 6% Ni, 4% Cu) having a TiN finish (e.g., 0.0002 in.). The distal end shield 38 may include a identification marking area 40 identify the number of channels (i.e., catheters 12) of the system with which the distal end shield 38 is to be used. Holes 68 may be provided for suturing the end shield 38 in place at the treatment site or for release of air upon insertion of the distal end 36 of the body 20 into the recessed area 74 of the distal end shield 38. Ends 72 may be rounded, e.g., to avoid sharp edges.

Figure 13:
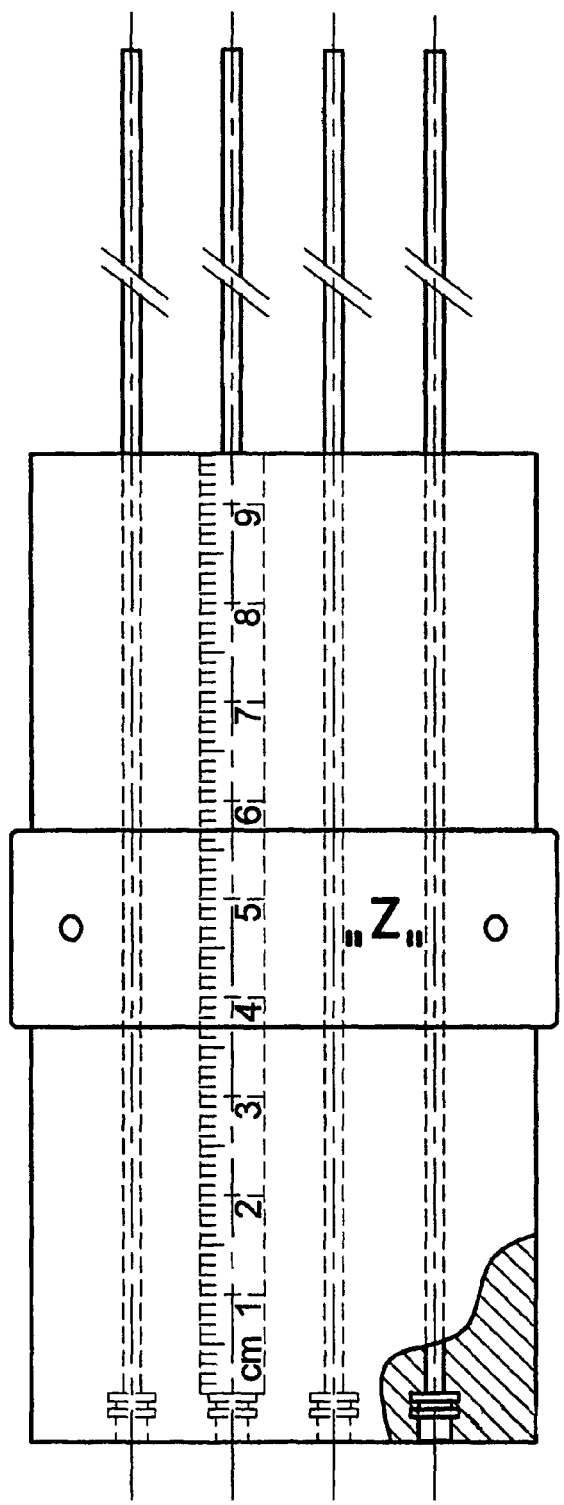
FIG. 13 is a top view of the system illustrated in FIG. 1 with the shield illustrated in FIGS. 9 and 10.

FIG. 13 illustrates the system 10 with the shield 22 provided on the body 20. The shield 22 is movable along the length of the body 20 to enable radiation attenuation when the catheters 12 are loaded with nuclear material. If the nuclear material is placed further along the catheters 12 (e.g., toward the proximal end 14) the movable shield 22 may be slid down the body to provide localized protection.

What is claimed is:

1. A system, comprising:
   a body;
   at least one catheter including a portion arranged within the body and extending along a longitudinal length of the body, each catheter including a blind lumen in which a radioactive material is insertable; and
   a shield arranged on an exterior of the body and movable along the body in a longitudinal direction of the catheter;
   wherein the at least one catheter includes a plurality of catheters arranged in a linear array along a width of the body; and
   wherein the shield includes a TiN finish.

2. The system according to claim 1, wherein the shield is formed of a tungsten material.

3. The system according to claim 1, wherein the catheters are equally spaced along the width of the body.

4. The system according to claim 1, wherein the body is formed of a synthetic material.

5. The system according to claim 1, further comprising an end shield arranged on a distal end of the body.

6. The system according to claim 5, wherein the end shield is formed of a tungsten material.

7. The system according to claim 1, wherein the catheter includes a tube portion plugged at a distal end.

8. The system according to claim 1, wherein the catheter is connectible to a loading device adapted to load the radioactive material into the catheter.

9. The system according to claim 1, wherein the body includes a scale arranged along the longitudinal length adapted to indicate a position of the shield along the longitudinal length.

10. A system, comprising:
a body;
at least one catheter including a portion arranged within the body and extending along a longitudinal length of the body, each catheter including a blind lumen in which a radioactive material is insertable;
a shield arranged on an exterior of the body and movable along the body in a longitudinal direction of the catheter; and
an end shield arranged on a distal end of the body;
wherein the end shield includes a TiN finish.

11. The system according to claim 10, wherein the at least one catheter includes a plurality of catheters arranged in a linear array along a width of the body.

12. The system according to claim 10, wherein the shield is formed of a tungsten material.

13. The system according to claim 10, wherein the shield includes a TiN finish.

14. The system according to claim 11, wherein the catheters are equally spaced along the width of the body.

15. The system according to claim 10, wherein the body is formed of a synthetic material.

16. The system according to claim 10, wherein the catheter includes a tube portion plugged at a distal end.

17. The system according to claim 10, wherein the catheter includes an anchor device at a distal end adapted to anchor the catheter in the body.

18. The system according to claim 10, wherein the catheter is connectible to a loading device adapted to load the radioactive material into the catheter.

19. The system according to claim 10, wherein the body includes a scale arranged along the longitudinal length adapted to indicate a position of the shield along the longitudinal length.

20. A system, comprising:
a body;
at least one catheter including a portion arranged within the body and extending along a longitudinal length of the body, each catheter including a blind lumen in which a radioactive material is insertable; and
a shield arranged on an exterior of the body and movable along the body in a longitudinal direction of the catheter;
wherein the at least one catheter includes a plurality of catheters arranged in a linear array along a width of the body; and
wherein the catheter includes an anchor device at a distal end adapted to anchor the catheter in the body.

21. A system, comprising:
a body;
at least one catheter including a portion arranged within the body and extending along a longitudinal length of the body, each catheter including a blind lumen in which a radioactive material is insertable;
a shield arranged on an exterior of the body and movable along the body in a longitudinal direction of the catheter; and
an end shield arranged on a distal end of the body;
wherein the at least one catheter includes a plurality of catheters arranged in a linear array along a width of the body; and
wherein the end shield includes a TiN finish.

* * * * *